United States Patent
Fink

(10) Patent No.: US 12,070,523 B2
(45) Date of Patent: Aug. 27, 2024

(54) SANITIZATION OF AN ARTICLE USING IN SITU ELECTROLYSIS

(71) Applicant: APPLIED BIOCIDE GMBH, Bönen (DE)

(72) Inventor: Michael Fink, Santa Clara, CA (US)

(73) Assignee: APPLIED BIOCIDE GMBH, Bönen (DE)

( * ) Notice: Subject to any disclaimer, the term of this patent is extended or adjusted under 35 U.S.C. 154(b) by 0 days.

(21) Appl. No.: 17/856,408

(22) Filed: Jul. 1, 2022

(65) Prior Publication Data
US 2024/0000984 A1    Jan. 4, 2024

(51) Int. Cl.
| | |
|---|---|
| *A61L 2/03* | (2006.01) |
| *A61L 2/16* | (2006.01) |
| *A61L 2/18* | (2006.01) |
| *A61L 101/06* | (2006.01) |
| *C02F 1/467* | (2023.01) |

(52) U.S. Cl.
CPC ............... *A61L 2/035* (2013.01); *A61L 2/16* (2013.01); *A61L 2/18* (2013.01); *C02F 1/4674* (2013.01); *A61L 2101/06* (2020.08); *A61L 2202/11* (2013.01); *A61L 2202/15* (2013.01)

(58) Field of Classification Search
CPC ... A61L 2/035; A61L 2/16; A61L 2/18; A61L 2101/06; A61L 2202/11; A61L 2202/15; C02F 1/4674; C25B 9/19
See application file for complete search history.

(56) References Cited

U.S. PATENT DOCUMENTS

| | | | | |
|---|---|---|---|---|
| 6,106,691 A | * | 8/2000 | Nakamura | ............. A61B 90/70 204/229.4 |
| 2016/0029639 A1 | * | 2/2016 | DiMascio | ................. C25B 1/16 424/661 |

FOREIGN PATENT DOCUMENTS

| | | | | |
|---|---|---|---|---|
| DE | 202008017160 U1 | 3/2009 | | |
| DE | 2428256 B1 | 10/2011 | | |
| EP | 2184075 B1 | 1/1976 | | |
| EP | 2509640 A1 | 6/2011 | | |
| EP | 2926710 A1 | 10/2015 | | |
| GB | 2429152 A * | 2/2007 | ............. | A61K 33/00 |
| WO | WO-9958164 A1 * | 11/1999 | ............. | A61L 2/035 |

OTHER PUBLICATIONS

Translation of JP-2013533925 published on Aug. 2013 (Year: 2013).*

* cited by examiner

*Primary Examiner* — Salil Jain
(74) *Attorney, Agent, or Firm* — Raj S. Dave; Dave Law Group LLC

(57) ABSTRACT

A system, comprising: a chlorine source in form of an electrolysis unit to generate an in-situ generated active chlorine; wherein a concentration of perchlorate is not more than half of a concentration of chlorate; and pH of a fluid containing in-situ generated active chlorine is more than 7.4; a buffer tank to store a concentrate of in-situ generated active chlorine as a free available chlorine (FAC); a fluid distribution system to supply FAC in form of an in-use fluid to the cabinet; wherein the system is configured to clean and disinfect an article with the fluid while complying with national and international standards for food safety, operator's safety and regulatory requirements regarding the use of biocides.

18 Claims, 6 Drawing Sheets

SANITIZATION OF AN ARTICLE USING IN SITU ELECTROLYSIS

FIELD OF THE INVENTION

This invention relates to a method and a system to sanitize the article using in situ electrolysis.

BACKGROUND OF INVENTION

The electrolysis of alkali chloride solutions by means of electrolytic cells has been a well-known practice for decades, most importantly for industrial-scale manufacturing of chlorine bleach, with the desired byproduct of sodium hydroxide and the option for subsequent burning of chlorine gas with hydrogen gas formed at the cathode, to obtain hydrochloric acid.

Small-scale electrolytic devices have become more and more popular over the last approximately 20 years, mainly a result of technological progress in the field of affordable but still reliable process control.

Smaller-scale chlorine electrolysis devices, which are operated on the site of chlorine use are available as well. Apart from some rare applications like waste-water treatment, chlorine from these devices is normally used for biocidal purposes, to control undesired or harmful microorganisms.

Low-chlorate electrolysis devices are also readily available, typically with separated electrolysis half-cells and an opportunity to withdraw or partly re-circulate both analyte and catholyte.

An even lower specific chlorate level can be achieved, but after scheduled process interruptions of up to 72 hours (for example over weekends), the situation in the batch tank holding the concentrate (which is usually level-operated and thereby guarantees a swift restart of the system after a longer interruption) might no longer be compliant with the maximum tolerable specific chlorate content on food contact materials treated without rinsing, and consecutively in processed food/feed.

The decomposition of in-situ generated chlorine solution is described to usually take place very rapidly, resulting in a loss of more than 50% of the available chlorine over a period of several days, accompanied by dramatically increasing chlorate concentrations.

These devices require expensive maintenance costs to maintain an ultra-low chlorate concentration. The split-cell devices are not practicable for de-centralized use, e.g. in very large industrial-scale applications or in horticulture.

It must be noted that a later adjustment of the pH of the electrolyte concentrate, or dilution is not permitted in the European Union—since it would not be covered by applicable drinking water specifications and treatment process requirements.

Further, regarding biocidal use of chlorine, the ones that are related to potential or incidental food contact are most important such as but not limited to Industrial food processing, animal husbandry, horticulture etc.

The active substance chlorine has been assessed for local effects only. The undissociated chlorine compound of the same oxidation state such as hypochlorous acid exhibits a significant vapor pressure which must be considered for inhalation hazard and risk for all biocidal uses. The present devices operating at a pH <7.5 would lead to an unacceptable exposure of operators to hypochlorous acid during the application, such as spraying, regardless of whether in an enclosure (cabinet) or an open spraying nozzle.

Larger-scale electrolytic devices are typically used for manufacturing storage stable aqueous solution with low chlorine content (typically <1 g/L FAC) and a pH below 7.4, which leads to the absolute predominance of undissociated hypochlorous acid. These solutions are usually manufactured and sold in the initial concentration range of 250 to 650 mg/L of active chlorine and are used in most cases without further dilution.

On the other hand, byproducts of concern in the context of food contact applications should also be observed carefully.

Chlorate, being a well-known pesticide is under scrutiny from regulators worldwide.

Perchlorate is the highest oxidized chlorine species possible. In fact, some of the systemic endpoints for chlorate have been taken from perchlorate animal studies. It is a well-known endocrine disruptor, an iodine antagonist, and is already under observation from some regulators, for example, the German Federal Risk Assessment Agency (BfR—Bundesinstitut für Risikobewertung).

At least in Europe, endocrine disrupting properties of substances are considered to be of non-threshold effects, which might end up in a zero-tolerance regulatory policy towards perchlorate residues in food or feeding stuff. Perchlorate is a non-threshold thyroid endocrine disruptor. According to European guidelines, compliance shall be confirmed by modelling dietary exposure for consumers (including toddlers) and comparison of (also combined) exposure with chlorate Maximum Residue Level (MRL) or Assigned Exposure Limit (AEL).

The available European food safety authority (EFSA)/European chemicals agency (ECHA) Guidance and bespoke models are required for assessment of dietary exposure. Non-compliance leads to a non-authorization decision and subsequent loss in marketability. Similar regulatory regimes exist in other countries also such as United States of America.

As a standard procedure in the United States, it is not allowed to treat/disinfect food with chlorine (FAC) solutions in the USA.

There are also massive concerns in some parts of the world, for example, in the European Union, regarding chlorine in contact with food.

This led to the requirement of a post-rinsing of the food material with drinking water in case high chlorine concentrations was used to disinfect tools that came in contact with food. It therefore required to compare the maximum amount of chlorine transferred e.g., a full carcass rinsed off with drinking water at the given maximum permitted drinking water chlorine concentration (a common and allowed practice), with the amount of chlorine transferred to a comparable piece of food (comparable in terms of surface to mass ratio) by the disinfected (and not rinsed) cutting tool.

These considerations resulted in the development of the most common use of a hot water/disinfectant bath. The tools to be disinfected are simply inserted/soaked in the hot water bath. This risks re-contamination with collected soil removed from treated surfaces that subsequently meets all devices treated in the same bath. The hot bath does not have beneficial effect of mechanical action in a spraying environment.

Further, in the hot water system, knives and other instruments used between the processing of the various carcasses must be disinfected at 82° C. hot water or an alternative system with at least similar effect. During this process, blood, fat, denatured protein, and lime accumulated on the blade producing foul smell and overall poor hygiene.

Economically also the hot water system has disadvantages. It requires high (almost double) volume of water, high energy demand for hot water supply, high maintenance costs, occupational safety concerns, scalding concerns, dulling of the blade due to fouling, and limescale build-up on the blade.

Disinfectants like lactic acid, peracetic acid, peroctanoic acid, etc. have been applied as disinfectants for tools at the concentration of 0.16% vol. Problems with such systems are that they are inefficient with beef because beef fat residues settle on the knife and the smell is foul, which is not acceptable to an operator.

Further, there is also a danger with corrosion due to high concentrations and long-term contact with the disinfectant in the slaughtering system.

In case of actual in-situ chlorine generation devices, which produce the active substance more or less in real time, there is less opportunity to include advanced technical features, due to the decentralized deployment of larger numbers of small-scale electrolysis units.

While there are a lot of opportunities to control the process (in terms of electrolysis parameters, pH, conductivity, buffer capacity of feed electrolyte and so on), when using electrolysis for the production of stable storage chlorine solutions at a pH of lower than 7.4, completely different conditions and system requirements exist in the field of actual in-situ generation of active chlorine for biocidal purposes. It has been observed that there is increase in chlorate content during long-term storage, up to 2 years, depending on the predominant pathway of chlorine decomposition, either by disproportionation into chlorite and chlorate, or by reductive decomposition into chloride with oxygen release.

Therefore, there is a long felt need for a process and system thereof, that is cost effective, easy to operate, less operator's exposure to harmful byproducts and efficient in disinfection.

SUMMARY OF INVENTION

In one embodiment, a system, comprising: a variable level-controlled chlorine batch tank; an electrolysis unit to generate an in-situ generated active chlorine; wherein a concentration of perchlorate is not more than half of a concentration of chlorate; and pH of a fluid containing in-situ generated active chlorine is more than 7.4; a buffer tank to store a concentrate of in-situ generated active chlorine as a free available chlorine (FAC); a cabinet; a fluid distribution system to supply FAC in the form of an in-use fluid to the cabinet; wherein temperature of the in-use fluid is less than 82° C.; wherein the system is configured to clean and disinfect an article with the fluid.

In an embodiment, pH of the system is about 7.5 to about 8.5.

In an embodiment, the concentration of perchlorate is about 0.01 mg/L.

In an embodiment, the cabinet is configured to place an article and expose the article to the in-use fluid.

In an embodiment, exposure time for the article is about less than 1 minute.

In an embodiment, the pH is achieved without use of a pH modifier to alter pH of a feed electrolyte.

In an embodiment, the pH is achieved without use of a pH modifier to alter pH of a chlorine concentrate.

In an embodiment, the pH is achieved due to presence of more than 50 Mol % of hypochlorite ion.

In an embodiment, the cabinet further comprises a fluid spraying nozzle.

In an embodiment, the temperature of the in-use fluid is in a range of about 30° C. to about 82° C.

In an embodiment, the temperature of the in-use fluid is less than or equal to 45° C.

In an embodiment, the cabinet comprises rotating brushes.

In an embodiment, a concentration of the FAC in the buffer is about 9 g/L, (calculated as Cl2).

In an embodiment, wherein the cleaning step fluid and the disinfecting step fluid are different.

In an embodiment, the system further comprises a diluting unit.

In an embodiment, the system is configured to reduce a microbial contamination less than a hot water basin system.

In an embodiment, the system is configured to reduce the microbial contaminant on the article to less than 1 CFU/cm$^2$.

In an embodiment, the system has application in a slaughterhouse.

In an embodiment, the article is a knife.

In an embodiment, the system is a single knife technology.

In an embodiment, the system could be used for a multiple knife technology (for example: two-knife technology).

BRIEF DESCRIPTION OF THE FIGURES

The patent or application contains at least one drawing executed in color. Copies of this patent or patent application, with drawing(s)/figure(s), will be provided by the Office upon request and payment of the necessary fee.

The figures are furnished with the application to understand the invention sought to be patented. The figures shall not be construed as the only way to perform the invention.

DETAILED DESCRIPTION

Definitions and General Techniques

Figure 1:
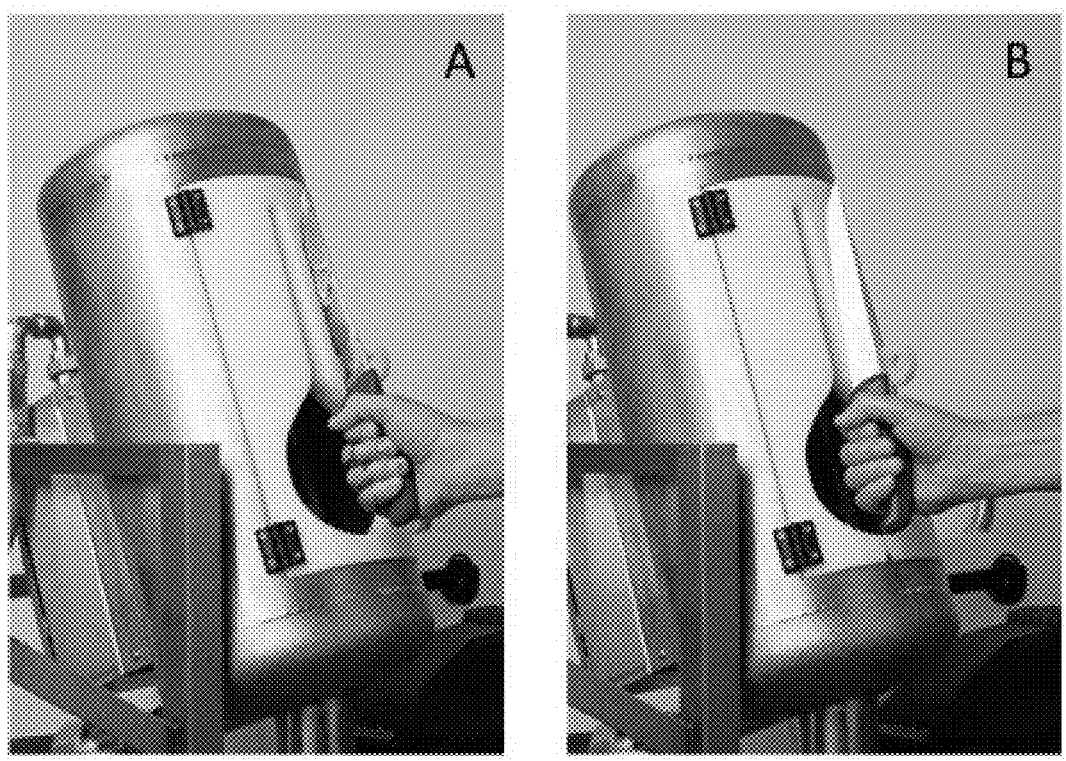
FIG. 1 provides a view of the cabinet and chamber and article before (FIG. 1A) and after the pre-rinsing/disinfection of an article, a cutting tool (FIG. 1B). Chamber produces in-situ and effective concentration of the product to be used for disinfection of tools such as knife, the cabinet is the portion that allows knife to be inserted inside the chamber and placed for the disinfection process.

For simplicity and clarity of illustration, the figures illustrate the general manner of construction. Descriptions and details of well-known features and techniques may be omitted to avoid unnecessarily obscuring the present disclosure. Additionally, elements in the figures are not necessarily drawn to scale. For example, the dimensions of some of the elements in the figures may be exaggerated relative to other elements to help improve understanding of embodiments of the present disclosure. The same reference numerals in different figures denotes the same elements.

The terms "first", "second", "third", "fourth", and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include" and "have" and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus.

The terms "left", "right", "front", "back", "top", "bottom", "over", "under", and the like in the description and in the claims, if any, are used for descriptive purposes and not necessarily for describing permanent relative positions. It is to be understood that the terms so used are interchangeable under appropriate circumstances, such that the embodiments of the apparatus, methods, and/or articles of manufacture described herein are, for example, capable of operation in other orientations than those illustrated or otherwise described herein.

No element, act, or instruction used herein should be construed as critical or essential unless explicitly described as such. Also, as used herein, the articles "a" and "an" are intended to include items and may be used interchangeably with "one or more". Furthermore, as used herein, the term "set" is intended to include items (e.g., related items, unrelated items, a combination of related items and unrelated items, etc.), and may be used interchangeably with "one or more". Where only one item is intended, the term "one" or similar language is used. Also, as used herein, the terms "has", "have", "having", and the like are intended to be open-ended terms. Further, the phrase "based on" is intended to mean "based, at least in part, on" unless explicitly stated otherwise.

The terms "couple", "coupled", "couples", "coupling", and the like should be broadly understood to refer to connecting two or more elements mechanically and/or otherwise. Two or more electrical elements may be electrically coupled together, but not be mechanically, or otherwise, coupled together. Coupling may be for any length of time, e.g., permanent or semi-permanent or only for an instant. "Electrical coupling" and the like should be broadly understood and includes electrical coupling of all types. The absence of the word "removably", "removable", and the like near the word "coupled", and the like, does not mean that the coupling, etc. in question is or is not removable.

As defined herein, two or more elements are "integral" if they are comprised of the same piece of material. As defined herein, two or more elements are "non-integral" if each is comprised of a different piece of material.

As defined herein, "real-time" can, in some embodiments, be defined with respect to operations carried out as soon as practically possible upon occurrence of a triggering event. A triggering event can include receipt of data necessary to execute a task or to otherwise process information. Because of delays inherent in transmission and/or in computing speeds, the term "real time" encompasses operations that occur in "near" real time or somewhat delayed from a triggering event. In a number of embodiments, "real time" can mean real time less a time delay for processing (e.g., determining) and/or transmitting data. The particular time delay can vary depending on the type and/or amount of the data, the processing speeds of the hardware, the transmission capability of the communication hardware, the transmission distance, etc. However, in many embodiments, the time delay can be less than approximately one second, two seconds, five seconds, or ten seconds.

The present invention may be embodied in other specific forms without departing from its spirit or characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

As defined herein, "approximately" or "about" can, in some embodiments, mean within plus or minus ten percent of the stated value. In other embodiments, "approximately" can mean within plus or minus five percent of the stated value. In further embodiments, "approximately" can mean within plus or minus three percent of the stated value. In yet other embodiments, "approximately" can mean within plus or minus one percent of the stated value.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, health monitoring described herein are those well-known and commonly used in the art.

The methods and techniques of the present invention are generally performed according to conventional methods well known in the art, and as described in various general and more specific references throughout the present specification unless otherwise indicated. The nomenclatures used in connection with, and the procedures and techniques of, embodiments herein, and other related fields described herein, are those well known and commonly used in the art.

The following terms and phrases, unless otherwise indicated, shall be understood to have the following meanings.

The term "chlorine source" is defined as a source that can provide chlorine or species of chlorine during electrolysis. The chlorine source could be all possible salt of chlorine which produce chlorine or chlorine species, for example sodium chloride solution (brine) or potassium chloride produce chlorine during electrolysis. The chlorine source can be in a storage box or tank that stores chlorine.

In an embodiment, the chlorine source can be in a variable chlorine batch tank or a buffer tank.

In an embodiment, chlorine can be free available chlorine which produced during electrolysis i.e., free available chlorine. Free available chlorine can be in the form of dissolved gas (Cl2), hypochlorous acid (HOCl), hypochlorite ion (OCl—).

In an embodiment, chlorine can be the inorganic chlorination byproducts which are chlorate (ClO3-) and perchlorate (ClO4-). Chlorate and perchlorate are the oxidation products of active chlorine species produced during electrolysis.

The term, "variable level-controlled chlorine batch tank" is defined as: a tank that holds and manages the chlorine concentrate such that a specific chlorate level is maintained in the tank at any time as well as when a reasonable start up time after process interruption is less than 12 hours. In an embodiment, the reasonable start up time after interruption is less than 10 hours, less than 8 hours, less than 6 hours, less than 4, less than 2 hours, less than an hour. An interruption time could be 24 hours, 48 hours, 72 hours, a week or more.

The term, "volume chlorine concentrate batch tank" refers to a tank has the function of ensuring a sufficiently long running time of the electrolysis unit, irrespective of the current demand, in order to provide stable production conditions and product quality in the electrolysis process. On the other hand, the tank provides chlorine solution (9.0 g/ltr) at any time to ensure inline dosing for supplying the spray units with 100-150 ppm chlorine solution.

The term, "electrolysis" is a technique that uses electric current to drive an otherwise non-spontaneous chemical reaction. The word "lysis" means to separate or break, so in terms, electrolysis would mean "breakdown via electricity." It may be used to produce gases via electrochemical reactions.

For example: the electrolysis of brine produces hydrogen and chlorine gases which bubble from the electrolyte and are collected. The initial overall reaction is thus:

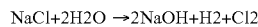
NaCl+2H2O →2NaOH+H2+Cl2

The reaction at the anode results in chlorine gas from chlorine ions:

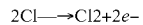
2Cl—→Cl2+2e-

The reaction at the cathode results in hydrogen gas and hydroxide ions:

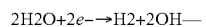
2H2O+2e-→H2+2OH—

Without a partition between the electrodes, the OH— ions produced at the cathode are free to diffuse throughout the electrolyte to the anode. As the electrolyte becomes more basic due to the production of OH—, less Cl2 emerges from the solution as it begins to react with the hydroxide producing hypochlorite at the anode:

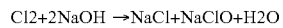
Cl2+2NaOH →NaCl+NaClO+H2O

The more opportunity the Cl2 has to interact with NaOH in the solution, the less Cl2 emerges at the surface of the solution and the faster the production of hypochlorite progresses. This depends on factors such as solution temperature, the amount of time the Cl2 molecule is in contact with the solution, and concentration of NaOH.

Likewise, as hypochlorite increases in concentration, chlorates are produced from them:

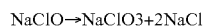
NaClO→NaClO3+2NaCl

Other reactions occur, such as the self-ionization of water and the decomposition of hypochlorite at the cathode, the rate of the latter depends on factors such as diffusion and the surface area of the cathode in contact with the electrolyte. In an embodiment, electrolysis of water will result in hydrogen and oxygen gas production.

The term, "electrolysis unit" or "electrolytic cell" or "electrochemical cell" or "electrolytic system" or similar are defined as a unit wherein electrolysis is carried out. An electrolysis cell has three components: an electrolyte and two electrodes (a cathode and an anode). In an embodiment, an electrolysis unit may have additional components such as but not limited to separators. The electrochemical unit provides a source of alkalinity or acidity in addition to an oxidizing agent. Different electrolyzers function in different ways, mainly due to the different type of electrolytic materials involved with them.

In an embodiment, an electrolytic system could be used for generation of oxidizing agents/products. In an embodiment, oxidizing products obtained from the electrolytic process provide a source of chlorine-based species. The oxidizing agents have numerous cleanings, sanitizing and/or antimicrobial capabilities. For example, the oxidizing agents are biocidal agents effective in killing bacteria, viruses, parasites, protozoa, molds, spores and other pathogens and are suitable for use according to the invention in a variety of washing systems.

The term, "in-situ" refers to, and translates literally to, "on site" or "in position". It can mean "locally", "on site", "on the premises", or "in place" to describe where an event takes place. For example: in chemistry, in-situ may mean "in the reaction mixture." Biocidal active substances are called in-situ generated active substances if they are generated from one or more precursors at the place of use.

The term "in-situ generated active chlorine" refers to production of chlorine by electrolysis of a chloride solution in the electrolysis unit, e.g., chlorine generated from sodium chloride or potassium chloride by electrolysis. Chlorine manufactured by the electrolysis of a sodium chloride solution (brine) or potassium chloride is known as the Chloralkali process. The Chlorine produced is highly reactive. Chlorate ($ClO_3-$) and perchlorate ($ClO_4-$) are important inorganic chlorination byproducts (CBPs). Chlorate and perchlorate are the oxidation products of active chlorine species produced during electrolysis. Chlorate and perchlorate were reported as products of mediated electro-oxidation that interact with, and degrade, contaminants.

In an embodiment, a concentration of perchlorate is not more than half of a concentration of chlorate in the product of mediated electro-oxidation. In an embodiment, concentration of perchlorate is less than 50%, less than 45%, less than 40%, less than 30%, less than 25% less than 20% concentration of the chlorate level in the product of mediated electro-oxidation reaction.

In an embodiment, concentration of perchlorate is less than 0.1 mg/L, less than 0.05 mg/L, less than 0.02 mg/L, 0.01 mg/L, less than 0.009 mg/L, less than 0.007 mg/L, less than 0.005 mg/L, less than 0.003 mg/L, less than 0.001 mg/L than in the in-use fluid.

In an embodiment, the generated chlorine is used locally at the site of its production.

The term, "concentrate" refers to a quantity of substance present in a unit amount of a mixture.

The term, "fluid" is defined as a substance, as a liquid or gas, that is capable of flowing and that changes its shape at a steady rate when acted upon by a force tending to change its shape. "In use fluid" is the fluid store in the fluid distribution system and containing free available chlorine. In use fluid flows inside the cabinet from the fluid distribution system.

The term, "cabinet" refers to a space or a room designed to insert an article for sanitization process and to remove the article after completion of the sanitization process.

The term "Free available chlorine" or "FAC" is the amount of chlorine available in water. This chlorine may be in the form of dissolved gas ($Cl_2$), hypochlorous acid (HOCl), or hypochlorite ion (OCl—) or other similar species of chlorine but does not include chlorine combined with an amine (ammonia or nitrogen) or another organic compound.

In an embodiment, concentration of FAC is more than 1 g/L, more than 1.5 g/L, more than 2 g/L, more than 2.5 g/L, more than 3 g/L, more than 3.5 g/L, more than 4 g/L, more than 4.5 g/L, more than 5 g/L, more than more than 5.5 g/L, more than 6 g/L more than 6.5 g/L, more than 7 g/L, more than 8 g/L, more than 9 g/L, more than 10 g/L or more in the in-use fluid.

The term, "fluid distribution system" is a term for distribution of desired fluid using a network of pipes. A network of pipes may have a loop structure to supply fluid from a place of the generation or storage of the desired fluid to the required area.

The term, "in-use fluid" is defined as a fluid containing FAC in distribution for sterilization of articles.

The term, "microbial contaminant" refers to presence of harmful chemicals and microorganisms which can cause illness to a consumer of that product. It includes pathogenic bacteria, viruses, or parasites, as well as prions (the agents of mad cow disease), and toxins.

The term "Disinfect" is a process that either removes or reduces or deactivates all forms of life (in particular referring to microorganisms such as fungi, bacteria, spores, unicellular, eukaryotic organisms such as plasmodium, etc.). Disinfection can be achieved through various means, including heat, chemicals, irradiation, high pressure, and filtration. In an embodiment, disinfection is achieved by a chemical means. Throughout the specification, different terms such as disinfection, sterilization and sanitization are interchangeably used and mean same as per this invention.

The term, "sanitization" means that as per European Regulation, an article that underwent a cleaning and disinfection process according to an embodiment of the present disclosed invention and is fit for human consumption.

The term, "clean" refers to an act to remove dirt, contamination, and impurities from the article. Therefore, an act of performing or aiding in soil removal, bleaching, microbial population reduction, or combinations thereof comes under the act of clean. Cleaning is different from disinfection in a way, because in cleaning majorly dirt, oil or similar are removed from the article. Cleaning does not kill the microbes though some microbes may be removed unintentionally in the process. Disinfection is a process where intentionally microbial count is reduced to an acceptable range for a human use.

In an embodiment, cleaning step may be followed by sanitization step. In an embodiment, cleaning and sanitization may be combined in a single step.

The term "Exposure time" is defined as a time span for which the operator or the article is exposed to some chemicals.

In an embodiment, the exposure time for an operator is less than a minute. As per present invention, an article is exposed to in-use fluid. In an embodiment, exposure time is less than 60 secs, less than 50 secs, less than 40 secs, less than 30 secs, less than 20 secs, less than 10 secs.

The term "pH modifier" are excipients used to adjust pH of a solution.

In an embodiment, pH modifier could be, but not limited to, soda ash, sodium hydroxide, sodium silicate, sodium phosphates, lime, sulfuric acid, and hydrofluoric acid, or similar. The addition of a base or an acid, rather than buffers, is generally recommended for pH adjustment.

In an embodiment, the present invention does not employ use of pH modifiers.

The term "fluid spray nozzle" is a device that facilitates dispersion of fluid into a form of spray. Nozzles are used for three purposes: to distribute a liquid over an area, to increase liquid surface area, and to create impact force on a solid surface.

The term, "dietary exposure" is determination of the chemical residues on a particular food or foods based on consumption data for the specified food or foods. In the most simplified form, a dietary exposure is defined as food consumption multiplied with food chemical concentration. The purpose of calculating dietary exposure to a given chemical or contaminant is so the estimated dietary exposure can be compared to a relevant health standard such as the acceptable daily intake (ADI), the acute reference dose (ARfD) or reference dose (RfD), or a level known to cause adverse effects in animal or human health studies. From this comparison, one can begin to assess the risk of adverse effects from a chemical or contaminant due to dietary exposure.

In an embodiment, spray nozzles can be categorized based on the energy input used to cause atomization and the breakup of the fluid into drops. Spray nozzles can have one or more outlets. A multiple outlet nozzle is known as a compound nozzle. Multiple outlets on nozzles are present on spray balls, which have been used in the brewing industry for many years for cleaning casks and kegs. Spray nozzles range from heavy duty industrial uses to light duty spray cans or spray bottles.

In an embodiment, spray nozzles are installed e.g., in the slaughter line at the workplaces.

The term "rotating brush" is used in conjunction with a machine that spin it on a cylinder or on a ring. This spinning motion cleans hard surfaces to be treated or articles that meet the brush's bristles. Further these rotating brushes provide a more mechanical way of cleaning action on the article. Rotating brushes can be manufactured in a variety of configurations, and they are usually made to be replaceable once the bristles wear out from too much use.

The term, sprayer is a device used to spray a liquid. Sprayers are usually integrated mechanical systems, that means they are composed of various parts and components that work together to achieve the desired effect, in this case, the projection of the spray of a fluid. This can be as simple as a hand sprayer attached to a bottle that is pumped and primed by a spring-lever, a tube, and vacuum-pressure; or as complex as a 150-foot reach boom sprayer with a list of system components that work together to deliver the spray fluid. For complex sprayers, common system components include: the spray nozzle, sometimes with a spray gun, fluid tank, sprayer pump, pressure regulators, valves and gaskets, and fluid plumbing. The sprayer pump can be just as important as the sprayer type itself as there are many sprayer pump design types with various construction materials, inlet/outlet sizes, and performance specifications. Common sprayer pump types include diaphragm, centrifugal, and roller pumps. Examples of general sprayer types include, but not limited to, a boom sprayer, Boomless sprayer nozzle, mist sprayer, three-point hitch sprayer, truck-bed sprayer, towing-hitch sprayer, utility task vehicle UTV sprayer, all-terrain vehicle ATV sprayer, spot sprayer, back-pack sprayer, or similar.

The term, "diluting unit" is the unit designed for diluting the solution to a predetermined concentration. For example, the diluting unit could be a source of water that can be used with the methods, systems, and apparatus of the present invention. Exemplary water sources suitable for use in the present invention include, but are not limited to, water from a municipal water source, drinking water, or private water system, and the like.

The term "feed electrolyte" is defined as a chemical that is introduced in the electrolytic cell to undergo electrolysis to produce the chlorine or desired chlorine species.

The term "a hot water basin system" is an appliance that holds a hot water. In a hot water basin, temperature of the water is between 80° C. to about 100° C.

The term "multi-knife technology" involves at least two knives. During the slaughtering process, instruments used in between the processing of the various carcasses must be disinfected. The first knife is sanitized in a hot water basin, while the second knife is used to cut. After that, the knife is replaced with a new knife for the second cut, and the used knife is sanitized in a hot water bath. For each cut, the procedure is repeated. In slaughterhouses in particular, it must be ensured that the means of treating slaughtering tools, such as knives, are constantly and reliably cleaned and decontaminated during the slaughtering process in order to avoid the transmission of pathogens from one carcass to another. For this purpose, the so-called multi-knife technology is used in the slaughterhouse: In this technology, the butcher opens a first animal with a first knife, which he then puts in a hot water basin. With a second knife, a second animal is opened, and then the second knife is put in the same hot water bath. A third animal is then opened with the first knife. Through the water bath, germs are to be killed and pollutions are diminished and so a transfer of germs from one animal to the next animal is to be prevented.

In an embodiment, multi-knife technology is also called as two-knife technology.

The term, "single knife technology" refers wherein same knife could be used for processing of the various carcasses and simultaneously being disinfected. Unlike multi-knife technology, there is no two knives wherein the first knife is sanitized in a hot water basin, while the second knife is used to cut. The process of processing carcass and disinfection of carcass is done simultaneously within span of seconds using same knife.

The term "article" is an object. In an embodiment, the article comprises a knife. The article may include knives, woven and non-woven fabrics, textiles, sinks, instruments, saws, axes, round knives, and the like.

The term "butchery" is the trade or business of a butcher wherein a butcher takes a section of meat and break them into small portions or custom cuts which can be sold to customers. The act of butchery is done in slaughterhouses.

The term "horticulture" is defined as the science and art of the development, sustainable production, of high-value, intensively cultivated food and ornamental plants.

The term "colony-forming unit (CFU or cfu)" is a measure of viable bacterial cells. In direct microscopic counts (cell counting using haemocytometer) where all cells, dead and living, are counted, but CFU measures only viable cells.

Counting with colony-forming units requires culturing the microbes and counts only viable cells, in contrast with microscopic examination which counts all cells, living or dead. The visual appearance of a colony in a cell culture requires significant growth, and when counting colonies it is uncertain if the colony arose from one cell or a group of cells. Expressing results as colony-forming units reflects this uncertainty.

The purpose of plate counting is to estimate the number of cells present based on their ability to give rise to colonies under specific conditions of nutrient medium, temperature, and time. Theoretically, one viable cell can give rise to a colony through replication. However, solitary cells are the exception in nature, and most likely the progenitor of the colony was a mass of cells deposited together. In addition, many bacteria grow in chains (e.g. *Streptococcus*) or clumps (e.g., *Staphylococcus*). Estimation of microbial numbers by CFU will, in most cases, undercount the number of living cells present in a sample for these reasons. This is because the counting of CFU assumes that every colony is separate and founded by a single viable microbial cell.

The term, "CFU/cm2" is the number of colonies formed per cm2 of surface

There are numerous influences on physical, chemical, biocidal and risk related properties of the active chlorine used for biocidal purposes: pH value, excess salinity, buffer capacity of the de-hardened water used for preparing the electrolyte.

Of these properties, the pH of the biocide solution is decisive both with concerns regarding operators' exposure towards hypochlorous acid (at a lower pH of <7.4) and for biocidal efficacy against target organisms, which is negatively affected by higher pH values (HOCl and Cl2, are the more reactive species, despite having the same Cl+1 oxidation state as the hypochlorite ion). Both operator safety and potential consumer exposure towards chlorate are pre-conditions that cannot be negotiated; however, microbiological efficacy is also an absolute prerequisite for e.g. successful registration and actual use in critical food-contact applications.

Table 1 gives an idea how pH and buffer capacity (determine the prevalence of a certain, initial pH) of electrolyzed chlorine solutions and the impact from unavoidable byproducts present are related to operators' exposure and safety, as well as to the legal requirements (or expectations) in terms of microorganism control.

TABLE 1 pH and buffer capacity of electrolyzed chlorine solutions and the impact of unavoidable byproducts on operators' exposure and safety

|  | Antimicrobial efficacy | $ClO_3$ formation upon storage, relative to chlorine present | Operator's risk |
|---|---|---|---|
| pH-value | +pH (More than 7.4 pH), less efficacy, higher concentration so longer contact time needed. | +pH, more $ClO_3$, decomposition process shifted from oxygen release to disproportionation at higher pH | +pH, less risk, no vapor from hypochlorous acid, only aerosol exposure towards an aqueous solution of a non-volatile ion. |
| Buffer capacity |  | high buffer capacity/ carbonate hardness negative, delays pH drop upon decomposition. |  |

A person skilled in the art would either lower the concentration and/or increase disinfectant temperature to overcome the shortcomings of the devices used in the state of the art. Further, in order to minimize operator exposure, a normal optimization procedure would start at lowering the in-use concentration of active chlorine, while simultaneously having to accept longer treatment times (which is highly unwanted in industrial food processing operations) and/or increase temperature in order to improve antimicrobial action of the active substance. While the reduction of concentration may be a beneficial impact on operators' exposure, the increase of temperature will lead to both increased operators' exposure due to a higher hypochlorous acid vapor pressure at elevated temperatures and increased problems with material compatibility of hot, aqueous chlorine solutions containing an excess of the precursor (alkali chlorides).

Alternatively, one might consider using treatment devices that have a lower formation rate of aerosol or vapor, compared to the highly efficient 2-phase spray nozzles used in present invention. These considerations further lead away from the disclosed state-of-the-art system, ending at the most common use of a hot water/disinfectant bath—where the tools to be disinfected are simply inserted/soaked, not having the beneficial effect of mechanical action in a two-phase spraying environment, and also risking re-contamination with collected soil removed from treated surfaces, that subsequently is in contact with all devices treated in the same bath.

In an embodiment of present invention, a reasonable start up time after process interruption is less than 12 hours. Process interruption could be scheduled process interruptions of up to 72 hours (for example over weekends). In an embodiment, the reasonable start up time after interruption is less than 10 hours, less than 8 hours, less than 6 hours, less than 4, less than 2 hours, less than an hour. An interruption time could be 24 hours, 48 hours, 72 hours, a week or more.

In an embodiment of the present invention, decomposition of in-situ generated chlorine solution is less than 50%, less than 40%, less than 30%, less than 25%, less than 20%, less than 10% of the available chlorine over a period of several days.

In an embodiment, there is no increase in chlorate content after storage time of 6 months, 1 year, 1.5 years. In an embodiment, increase in chlorate content is not more than 10%, 15%, 20%, 30%, 35%, 40% of the concentration that was present just before the storage time.

In an embodiment, storage time is 1 month, 3 months, 6 months, 1 year, 1.5 years or 2 years or more.

In an embodiment of present invention, perchlorate concentrations do not exceed half of chlorate concentration in the solution. In an embodiment, perchlorate concentration is less than 40%, less than 30%, less than 25%, less than 20% of the chlorate concentration in the solution.

In an embodiment, concentration of perchlorate is below the limit of detection (LOD) of the most recent High Performance Ion Chromatography systems.

In an embodiment, perchlorate is about 0.01 mg/L, less than 0.01 mg/L, less than 0.0075 mg/L, less than 0.005 mg/L or less than this in the total solution.

It is also important to consider that results of the novel disinfection process do match or exceed the results achieved by the standard 82° C. hot water bath treatment, currently established in e.g. most industrial meat processing plants.

In an embodiment of the present invention, disinfection of an article leads to decrease in microbial count less than 7 $CFU/cm^2$, 6 $CFU/cm^2$, 5 $CFU/cm^2$, 4 $CFU/cm^2$, 3 $CFU/cm^2$, 2 $CFU/cm^2$, 1 $CFU/cm^2$.

In an embodiment, disinfection with in-situ generated active chlorine at a pH, at site of use, of more than 7.4. The in-use solution may be diluted prior to being used.

In an embodiment, disinfection with in-situ generated active chlorine is achieved at a pH of more than 7.4. A pH of more than 7.4 is attained by using a diluted hypochlorite ion concentration of more than 50 Mol % hypochlorite ion. This is achieved without modifying the pH of the feed electrolyte/chlorine concentrated/diluted in-use solution in any way. On the contrary, in the prior art, disinfection was achieved either by lowering the pH to improve antimicrobial efficacy or lowering the initial and post storage specific chlorate concentrations.

In an embodiment, in-situ generated active chlorine is more than 50 Mol % of the hypochlorite ion. In an embodiment, in-situ generated active chlorine is more than 60 Mol %, more than 65 Mol %, more than 70 Mol %, more than 75 Mol %, more than 80 Mol %, more than 85 Mol % of the hypochlorite ion.

In an embodiment, this is achieved without pH-relevant modifications to the feed electrolyte/chlorine concentrated/diluted in-use solution.

This achievement is not obvious to a person skilled in the art because one would rather use a lower pH to a) improve antimicrobial efficacy, and (b) typically have lower initial (and post-storage—short term) for specific chlorate concentrations. Further, this only could be achieved with split-cell, low chlorate electrolysis devices.

In an embodiment, a standard open cell electrolysis device, which is usually used in swimming pool, Potable water, Process water or other applications, is employed in the system where the systemic/dietary exposure of consumers towards impurities such as chlorate is highly unlikely. On the contrary, in the prior art, the effect of a lower pH in the electrolyte and a much lower initial specific chlorate content is far less important than measures taken to maintain a compliant chlorate level in the batch tank (always feeding the dilution unit)—even after restart following a scheduled process interruption.

In an embodiment, a variable/dynamic level-controlled chlorine batch tank is used to guarantee both compliant specific chlorate levels as well as reasonable startup times after process interruptions. This is also not obvious, because there will be a certain start-up time required to operate under safe dietary conditions after a longer process interruption (e.g. >12 hours, compared to a single-level operated tank—always full). Implementation of a controlled, variable level tank is a technical feature one would try to avoid.

In an embodiment, the system comprises a mandatory two-step process, i.e., a cleaning step and a disinfecting step using disinfecting solution. This two-step process ensures that antimicrobial action takes place on an as-clean-as-possible surface and thereby allowing to assess antimicrobial efficacy under so-called (EN antimicrobial efficacy testing standards) "clean conditions", using less, or less impactful, soiling substances in the standard efficacy essays.

In an embodiment, the system comprises no pre rinse or post rinse step with different kinds of liquid medium in cleaning an article.

In an embodiment, the system comprises two-fluid spraying nozzles wherein the pressure is low to medium. Two-fluid spraying nozzle placed in a cabinet, wherein two-fluid spraying nozzle will provide the most intense contact between the disinfection solution and the hard surface to be treated, resulting in shorter treatment times and lower operator exposure.

In an embodiment, system comprises low to medium pressure 2-fluid spraying nozzles. Two-fluid spraying nozzle, placed in a suitable cabinet, will give the most intense contact between disinfectant solution and the hard surface to be treated, resulting in low treatment times and relatively moderate operators' exposure.

In an embodiment, the system further comprises revolving brushes to add more mechanical activity in the system.

In an embodiment, the system comprises rotating brushes for obtaining more mechanical action, but the problem is that rotating brushes may end up in severe microbiological problems on the surfaces of the brushing device and is not a viable option to further increase mechanical action.

In an embodiment, the temperature of in use fluid in the system is lightly elevated up to 45° C. The temperature of the in-use fluid is about 35° C., 40° C., 45° C., 50° C., 55° C., 60° C., 65° C.

In an embodiment, system allows short contact times such as less than 2 mins, less than 60 secs, less than 45 secs, less than 30 secs, less than 25 secs. Increasing aerosol formation, and vapor formation may not be significant as pH is more than 7.4.

In an embodiment, there is no presence of hypochlorous acid. In an embodiment, presence of hypochlorous acid is less than 1%, less than 0.5% concentration in the solution.

An embodiment relates to present in-situ chlorine processes.

An embodiment relates to a disinfection process that is applicable for all types of meat, for example, but not limited to, pork, beef, poultry.

Advantages of the present invention over state of art.

A mandatory 2-step disinfecting/cleaning step with disinfectant solution (no post- or pre-rinse/clean with different kind of liquid medium): This two-step process ensures that antimicrobial action takes place on an as-clean-as-possible surface and thereby allowing to assess antimicrobial efficacy under so-called (EN antimicrobial efficacy testing standards) "clean conditions", using less, or less impactful, soiling substances in the standard efficacy essays.

Low to medium pressure 2-fluid spraying nozzles: Two-fluid spraying nozzle, placed in a suitable cabinet, will give the most intense contact between disinfectant solution and the hard surface to be treated, resulting in low treatment times and relatively moderate operators exposure. Obtaining even more mechanical action by introducing e.g. a rotating brush, will end up in severe microbiological problems on the surfaces of the brushing device and is therefore not a viable option to further increase mechanical action.

A slightly elevated temperature up to 45 degrees: Shortening required contact times, not significantly increasing aerosol formation, and: Vapor does not have to be considered since pH >7.5 (no hypochlorous acid present).

In an embodiment, the disinfection process is applicable in all types of cutting processes. In an embodiment, the system could be used for all cutting tools, organ shells, hook hygiene, etc. Applicable in all types of cattle lines and modular concepts for any size of system web-based hygiene platform.

In an embodiment, the disinfection process is manual, automated, or a combination of manual and automation process.

In an embodiment, the disinfection process results in a lower microbial count on the article as compared to the 82° C. hot water system.

In an embodiment, the process involves a cleaning step.

In an embodiment, the process does not involve a rinsing step due to the residue profile.

In an embodiment, in using the electrolytic system, there is less amount of water consumed in the process, lower energy costs, and simpler improved work routines, and/or minimal changes, etc.

In an embodiment, the electrolytic system uses little floor space at the workplace and provides improved work safety.

In an embodiment, the sanitation process is a two-stage process with a cleaning stage and a disinfecting stage.

In an embodiment, the electrolytic system does not require a water basin. Therefore, there is no dirt accumulation.

In an embodiment, temperature of disinfection solution is around 40° C. In an embodiment, minimum temperature of the disinfection solution could be 30° C., 35° C., 40° C., 45° C., 50° C., and the maximum temperature of the solution could be 40° C., 45° C., 50° C., 55° C., ° C., 70° C. or more.

In an embodiment, the active substance is in-situ chlorine.

In an embodiment, the system has a biocidal effectiveness such as bactericidal and yeasticidal efficiency. It has a cleaning effect.

In an embodiment, the system uses two fluid technology for water saving and strong cleaning effect. In an embodiment, the system is easy to install and operate. We can use the same pipe system (if possible) and/or Air supply (both must be planned individually). In an embodiment, the system requires installation of a generator.

In an embodiment, the system provides an incomparable cleaning effect to the article, such as, but not limited to, a tool. The tool could be a knife, saw, axe, round knife used in automated poultry lines, and all types of automated cutting. In an embodiment, the system is used for sanitization of robots in the slaughter line and all types of automated cutting.

In an embodiment, the knife tip stands up vertically down in the chamber so there is no backflow of dirty water. The cut protection glove on the left hand can also be cleaned. The fluid has a mild temperature tolerable to human skin.

In an embodiment, the system has automated knife and hook washing stations.

In an embodiment, this system is not a multi-knife technology.

In an embodiment, the knife keeps the sharpness because there is no deposit of protein and lime on the knife.

In an embodiment, we are working at much lower temperatures compared to the hot water basin system at 82° C. It is impossible to hold the hand into the hot water basin without burning it. In the present invention, the fluid sprayed is around 40° C. which is below the melting point of the fat, for example pork fat or chicken or turkey fat, which is important in that the knife doesn't get slippery, which is the problem in the prior art where they use hot water in the rinsing bath.

In an embodiment, 35° C. to 40° C. water temperature, used in the present invention, is acceptable to an operator's hand.

In an embodiment, we compared the classical hot water basin system with the present invention to evaluate the resulting $CFU/cm^2$ remaining after disinfecting the article. The present invention had much lower $CFU/cm^2$, contaminates, on the article.

In an embodiment, the present invention saves a lot of water and energy costs, because to keep the water in a cold environment at 82° C. costs a lot of energy. And we have to replace water very rapidly in order to avoid buildup of extreme dirt in the basins.

In an embodiment, the system uses in-situ chlorine. In-situ chlorine has an advantage over using processed and delivered chlorine bleach; because such processed chlorine, when delivered and stored, develops more and more harmful species which are very bad for dietary risk assessment.

In an embodiment, in-situ chlorine reduces certain chlorine species.

In an embodiment, there is no water basin. Therefore, there is no accumulation of dirt in this electrolytic process.

In an embodiment, we are using a two-step system, that is a cleaning and a disinfection step. According to biocidal product regulation, cleaning is not enough using simple water. There has to be a cleaner or disinfection solution.

In an embodiment, in the system, time to expose an article to the fluid for sanitization is less than a minute. In an embodiment, time of exposure could be about 0.5 seconds, 1 second, 2 seconds, 3 seconds, 4 seconds, 5 seconds, 10 seconds, 20 seconds, 30 seconds, 45 seconds. In an embodiment, the article is exposed to the cleaning step and/or disinfecting step for less than a minute respectively. In an embodiment, the article is exposed to the cleaning step for about 1 second, 2 seconds, 3 seconds, 4 seconds, 5 seconds, 10 seconds, 20 seconds, 0.5 mins, 1 min, 2 mins, 3 mins, 4 mins, 5 mins. In an embodiment, the article is exposed to the disinfecting step for about 0.5 mins, 1 min, 2 mins, 3 mins, 4 mins, 5 mins.

In an embodiment, the system uses a disinfection solution for cleaning, it is convenient to run the cabinet, as we have, to install one pipe for the disinfecting solution, not two pipes for water and disinfecting solution, and so on.

In an embodiment, dirt is drained out using a few milliliters ml of the disinfection solution.

In an embodiment, the system is using two fluid technology. There is mixing of water and air to have a better mechanical effect and lower water demand, and this also allows the mechanical effect to obtain a better cleaning effect.

In an embodiment, the active substance is in-situ chlorine in the concentration of about 9.0 grams/liter.

In an embodiment, the disinfection solution contains an active substance in the range of about 100 ppm to 150 ppm. In an embodiment, the disinfection solution contains an active substance in a range of about 120 ppm to 170 ppm, 120 ppm to 160 ppm, 130 ppm to 150 ppm. In an embodiment, the minimum concentration of the active substance in the solution is 25 ppm, 30 ppm, 40 ppm, 50 ppm, 60 ppm, 70 ppm, 80 ppm, 90 ppm, 100 ppm; and the maximum concentration of the active substance in the solution is about 120 ppm, 130 ppm, 140 ppm, 150 ppm, 160 ppm, 170 ppm, 180 ppm, 190 ppm, 200 ppm.

In an embodiment, temperature of the solution is around 40° C.

In an embodiment, one step of cleaning is not allowed as per Europe Biocidal Regulation.

In an embodiment, inside the cabinet at the level of the hand there is a pressure plate and on the side several nozzles that produce the in-situ and effective concentration of the product diluted with the water.

In an embodiment, effectiveness of the intervention was tested in a field study by the Goldschmaus Group under real conditions for a total of 5 seconds for the cleaning and disinfection step in comparison to the 82° C. method.

Figure 2:
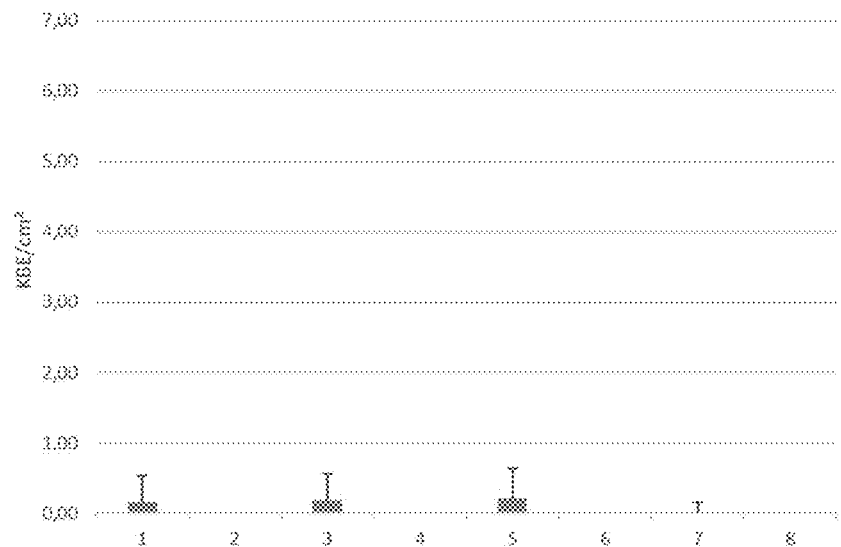
FIG. 2 shows an evaluation of contact samples after disinfection of the cutting tools with the in-situ chlorine system in comparison to 82° C. Sample rate is 50. Bar 1 shows CFU/cm$^2$, cfu/cm$^2$, KBE/g (KBE/g is a German translation of CFU/cm$^2$) measured on knife in contact with beef blood after disinfection by the in-situ system; Bar 3 CFU/cm$^2$ measured on knife used in cutting beef cattle fat after disinfection by the in-situ chlorine system; Bar 5 shows CFU/cm$^2$ measured on knife used in cutting pork after disinfection by the in-situ chlorine system; Bar 7 shows CFU/cm$^2$ measured on knife used in cutting pork belly fat after disinfection by the in-situ chlorine system.
Figure 3:
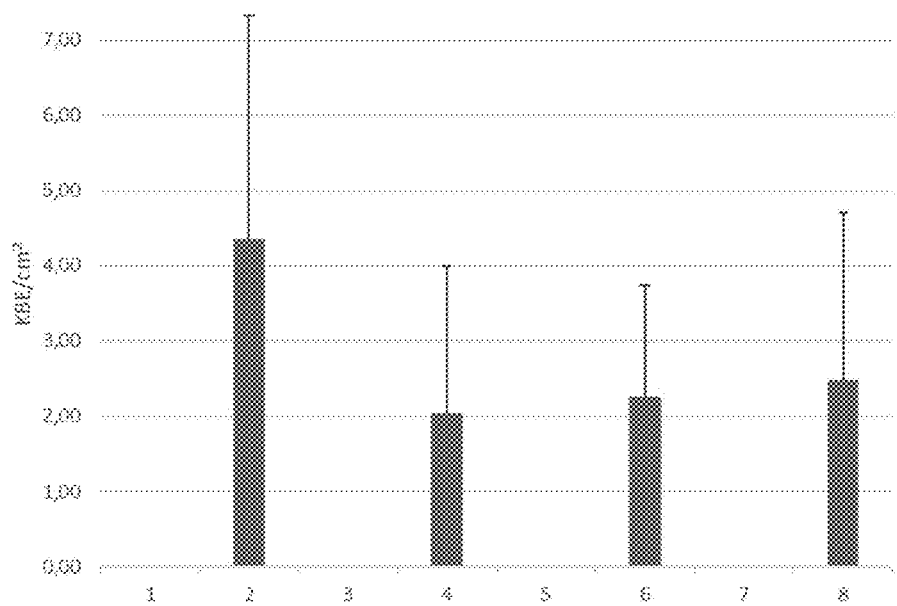
FIG. 3 shows an evaluation of contact samples after disinfection of the cutting tools with the 82° C. method. Sample rate is 50.2=CFU/cm$^2$ measured on knife in contact with beef blood after disinfection by the 82° C. method; 4=CFU/cm$^2$ measured on knife used in cutting beef cattle fat after disinfection by the 82° C. method; 6=CFU/cm$^2$ measured on knife used in cutting pork after disinfection by the 82° C. method; 8=CFU/cm$^2$ measured on knife used in cutting pork belly fat after disinfection by the 82° C. method.
Figure 4:
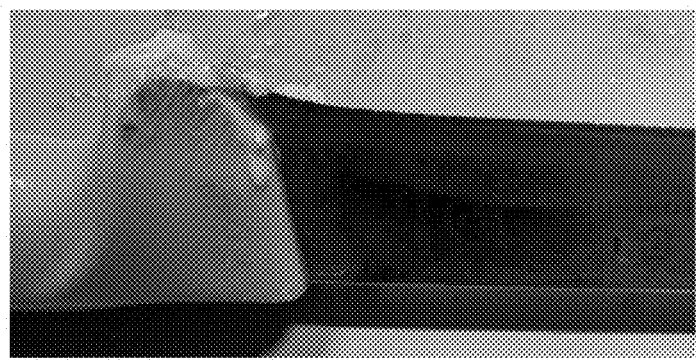
FIG. 4 provides a picture of a knife after being disinfected in a hot water basin in the 82° C. method.
Figure 5:
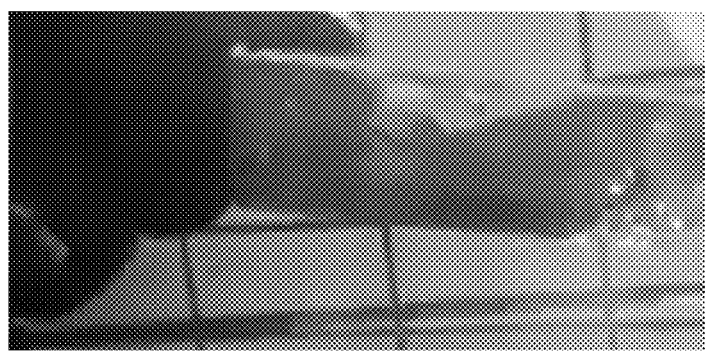
FIG. 5 provides a picture of a knife after being disinfected using the disclosed present invention.
Figure 6:
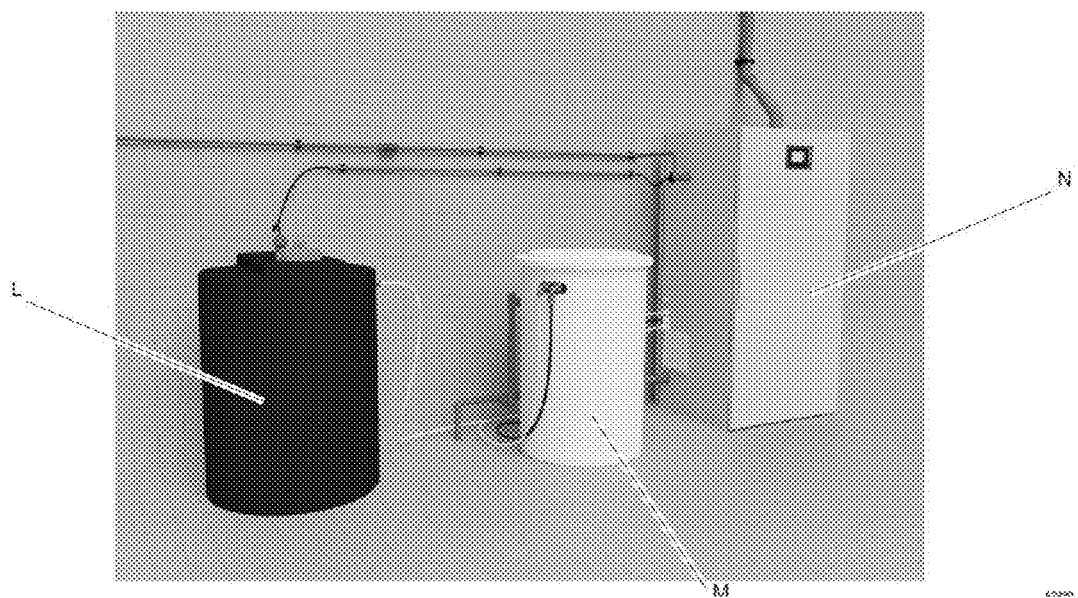
FIG. 6 provides arrangement of the system according to one embodiment of the present invention. Installation of ECA Generator; 'N' is an electrolysis unit, 'M' is a reservoir of a salt (Brine tank), 'L' is a storage tank for in-situ chlorine produced in the electrolysis. In an embodiment, L Storage tank FAC solution 9.0 gr/ltr FIG. 7 provides a chamber to insert knife for sanitization according to one embodiment of this invention.
Figure 7:
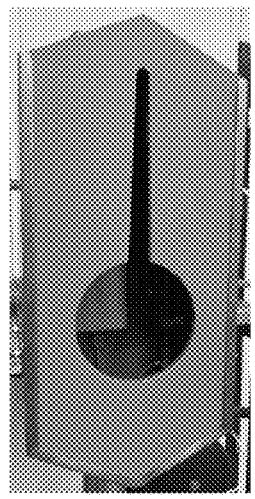
Figure 8:
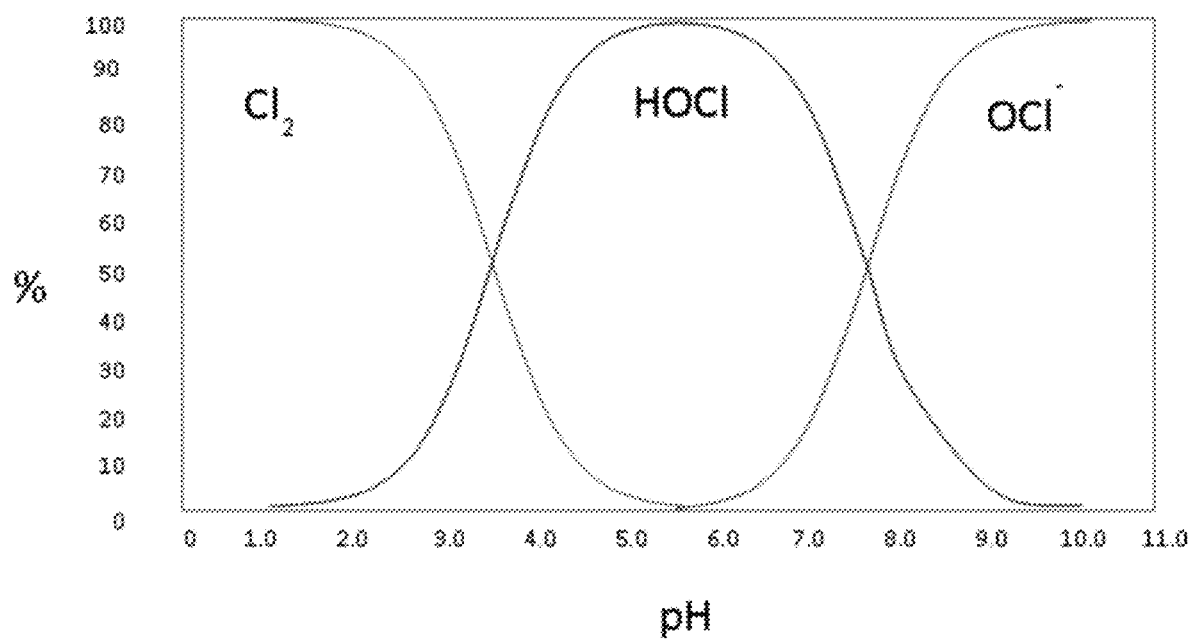
FIG. 8 shows effect of pH on proportion of chlorine in water. Green colour represents Cl2, blue colour represents hypochlorous acid (HOCl) and red colour represents hypochlorite ion OCl-1. It provides relationship between pH and proportion of chlorine in water. At pH of 7.4 and more, hypochlorite ion is dominant chorine species, whereas at pH less than 7 hypochlorous acid (HOCl) is dominant.
Figure 9:
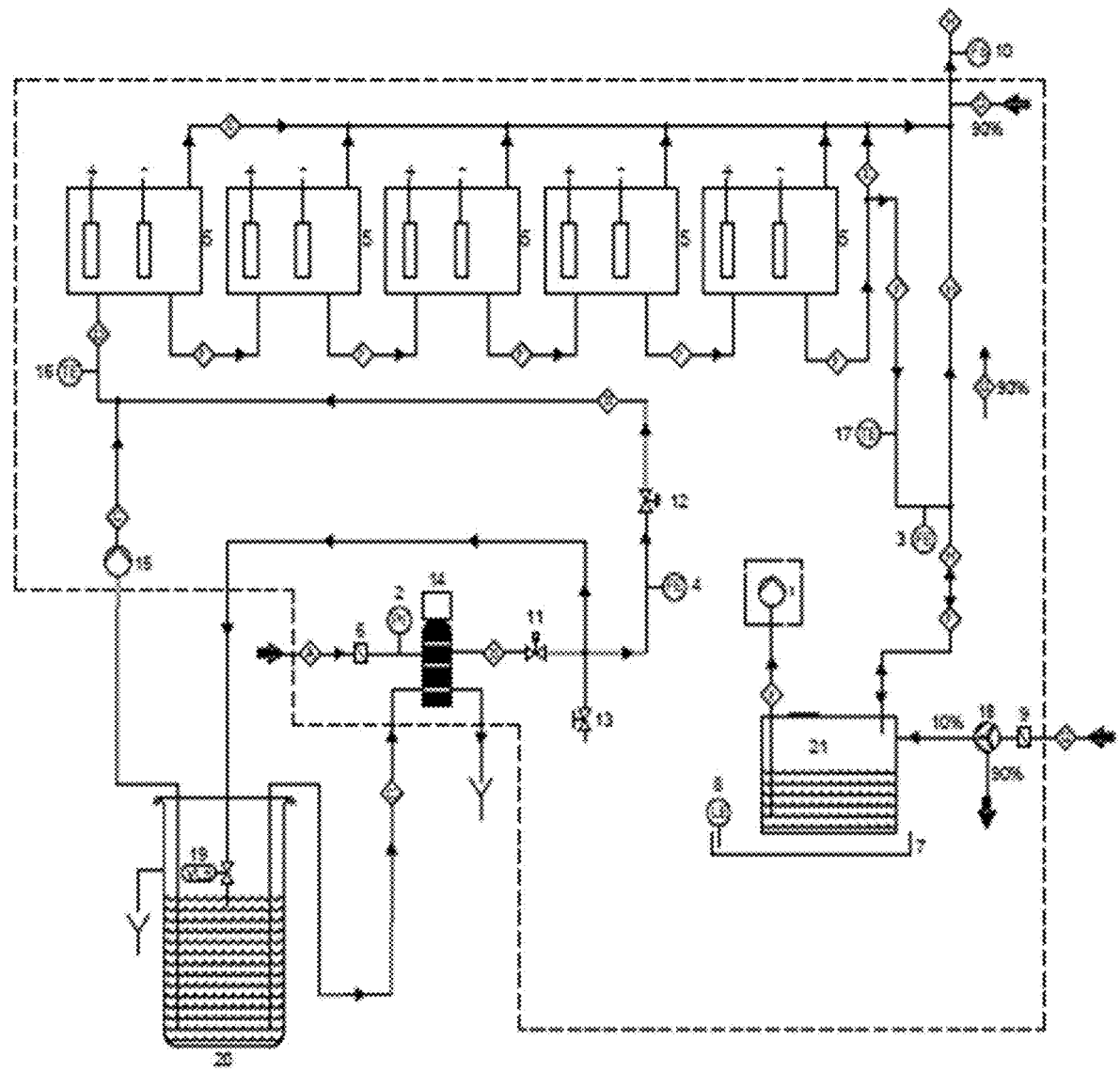
FIG. 9 provides a line drawing of a system providing information on brine preparation, pre-dilution, electrolysis device, buffer tank with controls, post-dilution distributing lines to e.g. cabinet or spray nozzle in a greenhouse etc. Different components of the system are indicated as: (1) for product metering pump (optional to be provided on site); (2) for pressure meter for potable water; (3) for flow meter for product from the cells; (4) for the flow meter softened water to the cells; (5) hypocells; (6) cartridge filler for potable water; (6) collecting pan; (7) collection pan; (8) liquid sensor for collecting pan; (9) air filter; (10) air flow sensor; (11) solenoid valve for softened water; (12) Control valve for softened water; (13) sampling tap for softened water; (14) softener; (15) brine metering pump; (16) temperature sensor for diluted brine to the cells; (17) temperature sensor for product to the cells ventilator; (18) ventilator; (19) float valve for brine storage tank (level controlled); (20) brine storage tank (with sodium chloride); (21) product storage tank, internal enclosed room system; A-potable water; B-softened water; C-saturated brine; D-Diluted brine; E-Hydrogen; F-product; G-Air; and H-Diluted hydrogen. [Ref: Assembly and operating instructions; Chlorine Electrolysis System; CHLORINSITU® IIa; ProMinent®]
Figure 10:
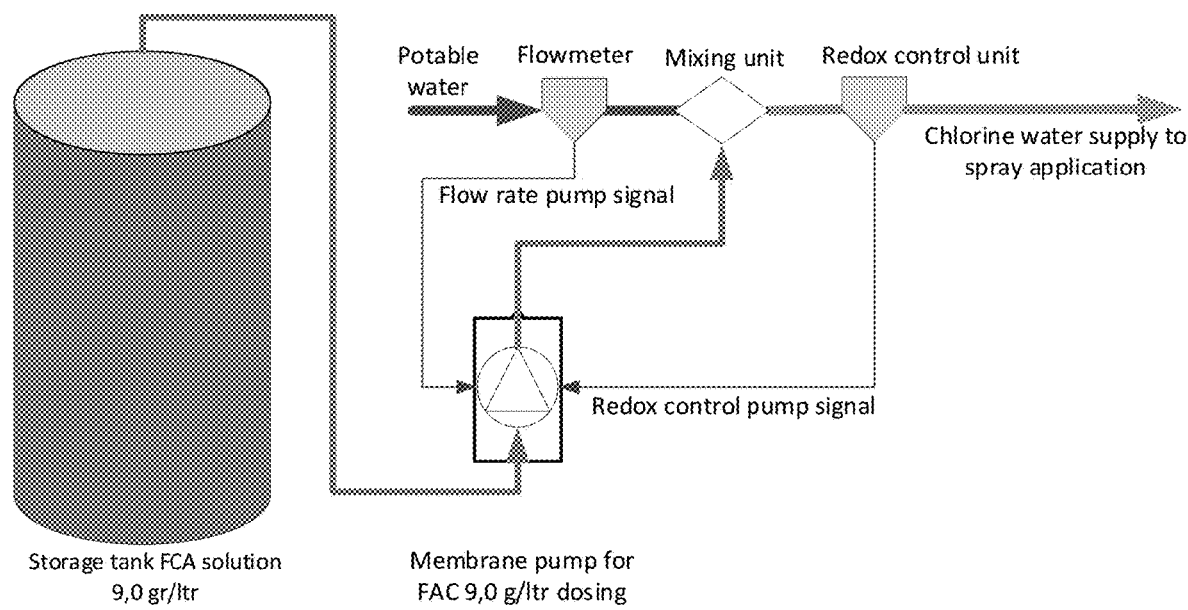
FIG. 10 provides Inline dosing system for chlorine water supply to spray application.

In an embodiment, after application the new method showed results in the range of 1-2 $CFU/cm^2$ (FIG. 2) on average on the cutting tool, whereas the 82° C. method showed results in the range of about 2-4 $CFU/cm^2$ (FIG. 3). In the 82° C. method, the remaining microorganisms on the tool are significantly higher compared to the new method of this invention. These results could be reproduced in other cattle lines. Therefore, the new method disinfects the tool better than the 82° C. method. In an embodiment, the $CFU/cm^2$ average on the cutting tool is less than 4, less than 3, less than 2, less than 1 or no CFU.

In an embodiment, the system disinfected the article with $CFU/cm^2$ count less than 2, less than 1. In an embodiment, the system completely disinfected the article with no colonies observed per $cm^2$.

In an embodiment, the field tests showed a high level of user acceptance of the electrolytic process, which can significantly improve slaughterhouse hygiene. Standardization of the entire electrolytic process, including the creation of automated records, is also possible.

In an embodiment, the in-situ chlorine technology presented here without rinsing requires proof of toxicological harmlessness of the remaining residues of the application solution on the cutting tool surfaces.

In an embodiment, for this purpose the remaining water volumes and the toxicologically relevant chlorine species were quantified and assessed in a so-called Dietary Risk Assessment (DRA) for adults and small children.

In an embodiment, cleaning and disinfecting with a solution.

In an embodiment, present invention has better economics, due to water and energy savings.

In an embodiment, present invention disinfects knife and guiding hand.

In an embodiment, present invention is suitable for cattle and in general high temperature melting fat.

In an embodiment, present invention produces no odor irritation at higher temperature In an embodiment, present invention fulfils the high standard hygiene demands of EU law for slaughtering hygiene In an embodiment, the new requirements of the International Food Standards IFS version 7 are implemented in a well-versed manner.

Regulatory Requirements with Regard to Impurity Residues in Food (EU)

According to standard Deutsches Institut für Normung (DIN) 901<5.4% Max $NaClO_3$ of FAC. (DIN (Deutsches Institut für Normung) 901 is the German "Chlorine for use in water treatment" standard, quoted in Biocidal Product Regulation Approval Decision for the active substance generated in-situ.)

Endpoints considered: ADI (allowable daily intake) chlorate (as $NaClO_3$): 0.003 mg/kg BW·day (equal to 0.0024 mg/kg BW·day as $ClO_3^-$), Arfd (acute reference dose) chlorate (as $NaClO_3$): 0.003 mg/kg BW·day (equal to 0.0024 mg/kg BW·day as $ClO_3^-$) (Source: EFSA), Maximum residue level (MRL) for chlorate; the smallest MRL from Commission Regulation (EU) 2020/749 has been used as a worst-case (0.05 mg/kg BW·day of chronic exposure towards chlorate).

Perchlorate is considered to be a non-threshold thyroid endocrine disruptor.

Compliance shall be confirmed by modelling dietary exposure for consumers (including toddlers) and comparison of (also combined) exposure with chlorate AEL.

The use of the available EFSA/ECHA Guidance and bespoke models is required for assessment of dietary exposure.

Non-compliance would lead to a non-authorization decision and subsequent loss in marketability. Similar regulatory regimes exist e.g., in the United States of America.

Perchlorate concentrations shall at least not exceed e.g., half of chlorate, ideally being below the LOD of the most recent High Performance Ion Chromatography systems (e.g., 0.01 mg/L $ClO^{4-}$).

It is also important to consider that results of the novel disinfection process do match or exceed the results achieved by the standard 82° C. hot water bath treatment, currently established in most industrial meat processing plants.

There are also massive concerns in some parts of the world, for example in the European Union, regarding chlorine in contact with food.

While a standard procedure in the United States, it is not allowed to treat/disinfect food with chlorine (FAC) solutions in Europe. This would lead to the requirement of a post rinse with drinking water, in case high chlorine concentrations are used to disinfect tools that come into contact with food.

It is therefore required to compare the maximum amount of chlorine transferred to e.g., a full carcass rinsed off with drinking water at the given maximum permitted drinking water chlorine concentration (a common and allowed practice), with the amount of chlorine transferred to a comparable piece of food (comparable in terms of surface to mass ratio) by the disinfected (and not rinsed) cutting tool.

WORKING EXAMPLE

Example 1: Slaughtering, Meat Processing

Investigation was done to study the advantages of the procedure compared to existing implementations serving the same purpose during its actual use with all types of meat.

The in-use temperature of up to 45° C., which is close to the melting point of a vertebrate fat, offers an excellent result for both fat residue cleaning and protein and blood residue cleaning, as these do not denature at this low temperature.

An optically free result, which means shiny bright stainless blades are obtained in fraction of seconds which is due to mechanical action of the two-substance nozzle with minimum water consumption and the arrangement in the cabinet. This surface condition is considered to be the optimum prerequisite for the subsequent disinfection step.

Limestone deposits on the blade, which are frequent in sterilizing tanks (where high temperatures reduce carbon dioxide solubility), do not exist at 45° C. This significantly extends the time between blade resharpening, which is a definite advantage.

In an embodiment, the saws, the nozzle arrangement and media supply are integrated into the unit. The regular cleaning intervals and mechanical assistance of the two-fluid nozzles remove not only the aforementioned fat and protein, but also tendon residues and bone meal, ensuring optimal preparation for the upcoming disinfection stage.

In an embodiment, operator will not notice any chlorine odour due to the high pH value of 7.5-8.5, and the low in-use concentration of 100-150 ppm FAC.

In an embodiment, system is equipped with a buffer tank for the concentrate (e.g. 9 g/L of FAC), from which the in-use solution for the supply of the cabinets and other points of use is produced by an inline dosing/dilution system. Un-treated tap-water is used for dilution.

In an embodiment, buffer tank also allows the electrolysis cell to run for a longer period of time in the optimal operating range with the lowest achievable oxidised chlorine by-products level (achievable with the electrolysis device chosen).

This is an elementary prerequisite for safely falling below the toxicological limits in the dietary risk assessment (DRA).

The measured surface microbial counts on various selective media show in most cases no findings.

Example 2: Packaging Cheese Slicer Department

Before packaging, many types of food are cut into portion-sized slices or pieces. For this purpose, slicers are used which are an integral part of the packaging line in order to keep the risk of contamination as low as possible during this hygienically sensitive process step. This process step takes place at very cool ambient temperatures. The cheese or similar kind of product is usually frozen or at least cooled strongly in order to have optimal mechanical properties during cutting. Due to the high hygiene requirements, the slicer and the packaging line have to be subject to periodical, intermediate disinfection.

For this purpose, cleaning and disinfection is carried out with the in-situ chlorine solution at a temperature of up to 45° C. The solution cools down on the cold cutting surface. The solution cools down very quickly on the cold machine parts, but the higher temperature ensures a very good initial cleaning and disinfection effect. The residual water is blown off with compressed air, so that after the process a dry surface is again available for the continuation of the packaging process.

Compared to the previously practiced method with highly concentrated alcohol solutions, the advantage is that the employees are not exposed to alcohol vapours, inducing drowsiness and associated risk for dangerous incidents. Furthermore, there is no danger of explosion from high airborne alcohol concentrations—no VOCs are emitted.

Example 3: Horticulture

In plant cultivation, both flowers and vegetables (tomatoes, peppers, etc.) are grown in large greenhouses with close stocking. In order to avoid microbial infections caused by bacteria, yeasts and moulds in these cultures, the plants must be constantly maintained by removing deceased plant parts. The scissors, knives and cutting tools must therefore be cleaned and disinfected in the cabinet using the two-substance nozzle method in order to avoid cross-contamination among the plants.

Dietary considerations have to be made (chlorate levels transferred by the cutting tool blades), be it for edible parts removed/harvested, or for withdrawn parts of the plants that end up in the (on-site) fertilizer cycle (compost treatment of biological waste).

Example 4: Human Health Assessment—Operator's Exposure Towards Airborne Chlorine When used according to one of the most envisaged use-areas (disinfection of cutting tools in industrial meat processing), the differences between the state-of-the-art (with low-chlorate and low-pH solutions) and present invention (with the use of high-pH (>7.5) low-medium chlorate hypochlorite solutions), the significance of strict pH-control—while still fulfilling efficacy requirements—becomes clearly visible.

Calculations of operator's exposure towards airborne FAC-species is based on the most recent EU Guidance and legislation and exposure assumptions, both are pointed out in the table 2 below:

Scenario: Soaking/spraying of cutting tools in industrial production—professional user, no Personal Protective Equipment (PPE) or Respiratory Protective Equipment (RPE) acceptable Model for dermal exposure: Semi-quantitative assessment Model for inhalation exposure: EU Commission and Agency Guidance: Technical notes for guidance (TNsG) spraying model 1 (Aerosol assessment) and HEAdhoc 16, 2 Compound Model I (Vapour assessment).

TABLE 2

The calculations of operator's exposure towards airborne FAC-species based on the most recent (2022) EU Guidance and legislation and exposure assumptions.

| Product details | Unit | Present invention | State of art |
| --- | --- | --- | --- |
| Active substance | | Permanent exposure over 8 hour shift, 160 applications/shift (every 3 mins.) Release Area (Tier-1): 1 m³ Active chlorine from OCl- (pH > 7.5) | Permanent exposure over 8 hour shift, 160 applications/shift (every 3 mins.) Release Area (Tier-1): 1 m³ Active chlorine from HOCl (pH < 7.4) |
| Equal to 100 mg/l in-use concentration FAC (as $Cl_2$) Local exposure | % | 0.01 | 0.01 |
| Dermal exposure | | Tier-1 | Tier-1 |
| Concentration in in-use dilution [active substance] | % | 0.01 | 0.01 |
| NOEAC dermal | % | 1.0 | 1.0 |
| % NOAEC dermal | % | 1.0 | 1.0 |
| Inhalation exposure - Aerosol | | Tier-1 | Tier-1 |
| Concentration in in-use dilution [active substance] | % | 0.01 | 0.01 |
| Indicative value (Module A4) | mg/m³ | 104 | 104 |
| Inhalation exposure [active substance] | mg/m³ | 0.0104 | |
| NOAEC (No Observed Adverse Effect Concentration) inhalation | mg/m³ | 0.5 | 0.5 |
| % NOAEC inhalation | % | 2.08 | 2.1 |

TABLE 2-continued

The calculations of operator's exposure towards airborne FAC-species based on the most recent (2022) EU Guidance and legislation and exposure assumptions.

| Inhalation exposure - Vapour | | Tier-1 | Tier-1 |
|---|---|---|---|
| Indicative value | mg/m$^3$ | 0.05466 | |
| Number of applications | /day | 160 | |
| Inhalation exposure [active substance] | mg/m$^3$ | 8.7456 | |
| NOAEC inhalation | mg/m$^3$ | 0.5 | |
| % NOAEC inhalation | % | 1749.12 | |
| Total inhalation exposure - Aerosol + vapour (below pH 7.4) | | Tier-1 | Tier-1 |
| Total inhalation exposure [active substance] | mg/m$^3$ | 8.756 | 0.0104 |
| NOAEC inhalation | mg/m$^3$ | 0.5 | 0.5 |
| % NOAEC inhalation | % | 1751.2 | 2.08 |

Calculations demonstrate that the use of high-pH hypochlorite solutions is perfectly safe, both for dermal and inhalation exposure (aerosols), even if (realistically) permanent operator's exposure over an 8 hrs shift is assumed (total dermal+inhalation approx. 3% of NOAEC (FAC)).

If, according to the state-of-the-art, a low-chlorate FAC solution with a pH below 7.4 is used, un-dissociated hypochlorous acid is the predominant chlorine species. Its significant vapour pressure leads to a mandatory consideration of a HOCl vapour assessment—and consequently to a 17-fold exceedance of the NOAEC (1,750%).

It is clear, that even less conservative assumptions regarding actual exposure time of operators will not lead to safe conditions.

The same is true for lowering the in-use concentration somewhat (which might be feasible, due to better FAC efficacy at lower pH values at identical $Cl_2$-concentration), the level of exceedance is simply too large to be compensated by realistic refinements of exposure assumptions.

Conclusion: Albeit exhibiting a potentially higher initial specific chlorate content and being less efficacious towards target organisms (at a given FAC concentration), the use of the high-pH solution according to the invention proves to be required—in order to fulfil human health considerations from EU (or US FDA, EPA) Regulators.

SUMMARY OF EXAMPLES—ADVANTAGES OF INVENTION

In an embodiment, a system/process comprising a commercially available (preferably open-cell) chlorine electrolysis device, a variable-level operated batch tank to hold and manage the chlorine concentrate, an in-line (tap water) dilution and liquid transport unit and a spraying cabinet with 2-phase fluid nozzles, to drain, designed for carrying-out a 2-step, combined cleaning and disinfection process on surfaces of cutting tools (non-rinse). These tools come into contact with food/feeding stuff and the whole setup is configured to provide compliant antimicrobial efficacy results, while observing allowable (dietary) levels of toxicologically relevant by-products (chlorate, perchlorate) remaining on cutting tool surfaces and simultaneously ensuring shortest treatment times—with the least level of operator's exposure towards hypochlorous acid vapor.

In an embodiment, the process is suitable for all cutting and sawing operations in the entire slaughter and primal cutting process, whether performed manually or automatically, in red and white meat.

In an embodiment, automated operations in pig or cattle slaughtering, such as splitting robots, the two-substance nozzle can be integrated into the cleaning cabinet of the respective machine.

In an embodiment, in poultry slaughtering lines, the process is integrated in the rotary machines—such as the vent cutter, evisceration or neck cracker.

In an embodiment, the system may also be used in transport hygiene such as the hook wash and the conveyor belts of the integral logistics.

In an embodiment, another field of application is the intermediate cleaning and disinfection in slicer lines for meat, vegetarian and cheese products.

In an embodiment, the system or process may also be used for the hygiene of cutting and processing equipment of fruit and vegetable products, particularly on ready-to-eat process lines.

In an embodiment, the system or process may also be used for the intermediate hygiene of tools for cutting and treating the plants in the horticulture. To avoid cross contamination while removing ill or contaminated parts of the plant, the tools have to be kept in a very high sanitation level—while ensuring a flexible operation in large greenhouses and an acceptable level of chlorine by-product contamination in this (also) non-rinse application.

All references, including granted patents and patent application publications, referred herein are incorporated herein by reference in their entirety.

What is claimed is:
1. A system, comprising:
(a) a reservoir of a chlorine source,
(b) an electrolysis unit,
(c) a storage tank, and
(d) a fluid distribution system,
wherein the chlorine source is configured to be fed into the electrolysis unit to generate a solution having an in-situ active chlorine comprising free available chlorine (FAC),
wherein the storage tank is configured to store the solution, wherein the fluid distribution system is configured to distribute the solution to a point of use;
wherein the solution at the point of use has:
- (i) a concentration of perchlorate not more than half of a concentration of chlorate;
- (ii) pH about 7.5 to about 8.5;
- (iii) more than 50 Mol % of the FAC as hypochlorite ion;
- (iv) a concentration range of the FAC more than 1 g/L to about 10 g/L; and
- (v) less than 1 Mol % of the FAC as hypochlorous acid;

wherein the system is configured to: a) reduce a microbial contaminant from an article exposed to the solution at the point of use for a particular time having temperature between about 30° C. to about 60° C., such that the microbial contaminant remaining after treatment is less than that of the microbial contaminant remaining on the article after being exposed to a hot water basin system for the same particular time and having temperature of a fluid in the hot water basin system between about 80° C. to about 100° C.; and b) avoid cross contamination between items cut using the article sterilized by the solution at the point of use.

2. The system of claim 1, further comprising a variable level-controlled chlorine batch tank configured to store a chlorine concentrate generated from the electrolysis unit such that a specific level of the chlorate in the chlorine concentrate is maintained.

3. The system of claim 1, wherein the concentration of the perchlorate is about 0.02 to 0.001 mg/l in the solution at the point of use.

4. The system of claim 1, wherein the particular time is less than 1 minute.

5. The system of claim 2, wherein the pH of the solution is achieved without use of a pH modifier to alter pH of a feed electrolyte.

6. The system of claim 1, wherein the temperature of the solution at the point of use is about 30° C. - about 50° C.

7. The system of claim 1, wherein a concentration of the FAC calculated as chlorine in the solution stored in the storage tank is about 9 g/L.

8. The system of claim 1, wherein the microbial contaminant on the article after being exposed to the solution for less than a minute decreases to less than 2 $CFU/cm^2$.

9. The system of claim 1, wherein the electrolysis unit is an open cell electrolysis unit.

10. The system of claim 1, wherein an operator exposure to inorganic chlorine species during usage of the solution at the point of use in a working shift, of about 8 hours and 160 applications, wherein each application is about 3 mins, has no observed adverse effect concentration (NOAEC) of about 0.5 $mg/m^3$.

11. A fluid having a concentration of perchlorate not more than half of a concentration of chlorate in the fluid and a pH between about 7.5 and about 8.5, and wherein the free available chlorine (FAC) of the fluid in a form of hypochlorite ion is greater than or equal to 50% of the FAC in total, and the FAC in a form of hypochlorous acid is less than 1% of the FAC in total.

12. The fluid of claim 11, wherein the fluid does not have a pH modifier.

13. The fluid of claim 11, wherein a concentration of the FAC at the point of use is about 10 g/l or less.

14. The fluid of claim 11, wherein an operator exposure to inorganic chlorine species during usage of the solution at the point of use in a working shift of about 8 hours and 160 applications with each application about 3 mins long, has no observed adverse effect concentration (NOAEC) of about 0.5 $mg/m^3$.

15. The system of claim 1, wherein the solution at the point of use is free of hypochlorous acid.

16. The fluid of claim 11, wherein the fluid is free of hypochlorous acid.

17. The fluid of claim 11, wherein the concentration of perchlorate is about 0.01 mg/L.

18. The system of claim 1, wherein the concentration of perchlorate is about 0.01 mg/L.

* * * * *